United States Patent
Kersey et al.

(10) Patent No.: US 7,389,187 B2
(45) Date of Patent: Jun. 17, 2008

(54) APPARATUS AND METHOD USING AN ARRAY OF ULTRASONIC SENSORS FOR DETERMINING THE VELOCITY OF A FLUID WITHIN A PIPE

(75) Inventors: Alan D. Kersey, South Glastonbury, CT (US); Daniel L. Gysling, Glastonbury, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 10/756,977

(22) Filed: Jan. 13, 2004

(65) Prior Publication Data

US 2004/0199340 A1 Oct. 7, 2004

Related U.S. Application Data

(60) Provisional application No. 60/531,065, filed on Dec. 19, 2003, provisional application No. 60/524,066, filed on Nov. 21, 2003, provisional application No. 60/447,498, filed on Feb. 14, 2003, provisional application No. 60/440,014, filed on Jan. 14, 2003, provisional application No. 60/439,715, filed on Jan. 13, 2003.

(51) Int. Cl.
*G01F 23/00* (2006.01)
(52) U.S. Cl. .......................................... 702/45
(58) Field of Classification Search ............. 702/45, 702/48, 50, 72; 600/300, 323, 505, 443, 600/437; 482/148, 8; 73/1.16, 861
See application file for complete search history.

(56) References Cited

U.S. PATENT DOCUMENTS 2,874,568 A  2/1959  Petermann
3,715,709 A  2/1973  Zacharias et al.
3,751,979 A  8/1973  Ims
3,781,895 A  12/1973 Monser
3,851,521 A  12/1974 Ottenstein
3,885,432 A  5/1975  Herzl
3,952,578 A  4/1976  Jacobs (Continued)

FOREIGN PATENT DOCUMENTS

EP      0290336      11/1988

(Continued)

OTHER PUBLICATIONS

Acoustic definition, Retrieved from the Internet: <http://www.m-w.com/dictionary/acoustic>.*

(Continued)

*Primary Examiner*—Tung S Lau

(57) ABSTRACT

An apparatus and method for measuring the flow velocity of a fluid flowing through a pipe that includes an array of at least two ultrasonic sensor units (with as many as 16 sensor units) disposed at predetermined locations along the pipe. Each sensor unit includes an ultrasonic transmitter and an ultrasonic receiver. Each sensor unit provides a respective signal indicative of a parameter of the transit time or amplitude of the ultrasonic signal propagating between each respective ultrasonic transmitter and ultrasonic receiver. A signal processor defines a convective ridge in the k-ω plane in response to the ultrasonic signals using an adaptive beamforming algorithm, such as Capon and Music. The signal processor further determines the slope of at least a portion of the convective ridge to determine the flow velocity of the fluid.

15 Claims, 12 Drawing Sheets

U.S. PATENT DOCUMENTS

| | | | |
|---|---|---|---|
| 4,004,461 A | 1/1977 | Lynworth | 73/861.27 |
| 4,032,259 A | 6/1977 | Brown | |
| 4,048,853 A | 9/1977 | Smith et al. | 73/861.25 |
| 4,080,837 A | 3/1978 | Alexander et al. | 73/61.45 |
| 4,195,517 A | 4/1980 | Kalinoski et al. | 73/461.27 |
| 4,248,085 A | 2/1981 | Coulthard | 73/861.06 |
| 4,320,659 A | 3/1982 | Lynnworth et al. | |
| 4,445,389 A | 5/1984 | Potzick et al. | 73/861.27 |
| 4,520,320 A | 5/1985 | Potzick et al. | |
| 4,561,310 A | 12/1985 | Barnard et al. | |
| 4,677,305 A | 6/1987 | Ellinger | |
| 4,717,159 A | 1/1988 | Alston et al. | |
| 4,896,540 A | 1/1990 | Shakkottai et al. | 73/861.02 |
| 4,932,262 A | 6/1990 | Wlodarczyk | |
| 5,040,415 A | 8/1991 | Barkhoudarian | 73/861.03 |
| 5,060,506 A | 10/1991 | Douglas | |
| 5,083,452 A | 1/1992 | Hope | 73/61 R |
| 5,218,197 A | 6/1993 | Carroll | 250/227.19 |
| 5,285,675 A | 2/1994 | Colgate et al. | 73/23.2 |
| 5,289,726 A | 3/1994 | Miau et al. | |
| 5,359,897 A | 11/1994 | Hamstead et al. | |
| 5,363,342 A | 11/1994 | Layton et al. | |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,625,140 A | 4/1997 | Cadet et al. | |
| 5,708,211 A | 1/1998 | Jepson et al. | |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,856,622 A | 1/1999 | Yamamoto et al. | 73/861.28 |
| 5,948,959 A | 9/1999 | Peloquin | 73/1.83 |
| 6,016,702 A | 1/2000 | Maron | |
| 6,151,958 A | 11/2000 | Letton et al. | 73/61.79 |
| 6,202,494 B1 | 3/2001 | Ricbel et al. | 73/861.29 |
| 6,233,374 B1 | 5/2001 | Ogle et al. | |
| 6,261,232 B1* | 7/2001 | Yokosawa et al. | 600/443 |
| 6,345,539 B1 | 2/2002 | Rawes et al. | |
| 6,349,599 B1 | 2/2002 | Lynnworth et al. | |
| 6,354,147 B1 | 3/2002 | Gysling et al. | 73/61.79 |
| 6,378,357 B1 | 4/2002 | Han et al. | 73/54.41 |
| 6,397,683 B1 | 6/2002 | Hagenmeyer | 73/861.18 |
| 6,412,353 B1 | 7/2002 | Kleven et al. | |
| 6,435,030 B1 | 8/2002 | Gysling et al. | 73/587 |
| 6,442,996 B1 | 9/2002 | Thurston et al. | |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,532,827 B1 | 3/2003 | Ohnishi | 73/861.27 |
| 6,536,291 B1 | 3/2003 | Gysling et al. | 73/861.42 |
| 6,550,342 B2 | 4/2003 | Croteau et al. | 73/800 |
| 6,558,036 B2 | 5/2003 | Gysling et al. | 374/147 |
| 6,587,798 B2 | 7/2003 | Kersey et al. | 702/50 |
| 6,601,005 B1 | 7/2003 | Eryurek et al. | |
| 6,601,458 B1 | 8/2003 | Gysling et al. | 73/861.04 |
| 6,609,069 B2* | 8/2003 | Gysling | 702/48 |
| 6,658,945 B1 | 12/2003 | Kleven | |
| 6,672,163 B2 | 1/2004 | Han et al. | |
| 6,691,584 B2 | 2/2004 | Gysling et al. | 73/861.42 |
| 6,698,297 B2 | 3/2004 | Gysling | 73/861.63 |
| 6,732,575 B2 | 5/2004 | Gysling et al. | 73/61.79 |
| 6,773,603 B2 | 8/2004 | Moorehead et al. | |
| 6,782,150 B2 | 8/2004 | Davis et al. | 385/12 |
| 6,813,962 B2 | 11/2004 | Gysling et al. | 73/861.26 |
| 6,837,098 B2 | 1/2005 | Gysling et al. | 73/61.79 |
| 6,837,332 B1 | 1/2005 | Rodney | |
| 6,862,920 B2 | 3/2005 | Gysling et al. | 73/61.79 |
| 6,889,562 B2 | 5/2005 | Gysling et al. | 73/861.42 |
| 6,898,541 B2 | 5/2005 | Gysling et al. | 702/100 |
| 6,971,259 B2 | 12/2005 | Gysling | |
| 6,988,411 B2 | 1/2006 | Gysling et al. | |
| 7,032,432 B2 | 4/2006 | Gysling et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0006409 A1 | 1/2004 | Liljenberg et al. | |
| 2004/0011141 A1* | 1/2004 | Lynnworth | 73/861.27 |
| 2004/0016284 A1 | 1/2004 | Gysling et al. | |
| 2004/0069069 A1 | 4/2004 | Gysling et al. | |
| 2004/0074312 A1 | 4/2004 | Gysling | |
| 2004/0144182 A1 | 7/2004 | Gysling et al. | |
| 2004/0167735 A1 | 8/2004 | Rothman et al. | |
| 2004/0168522 A1 | 9/2004 | Bailey et al. | |
| 2004/0168523 A1* | 9/2004 | Fernald et al. | 73/861.01 |
| 2004/0194539 A1 | 10/2004 | Gysling | |
| 2004/0199340 A1 | 10/2004 | Kersey et al. | |
| 2004/0199341 A1 | 10/2004 | Gysling et al. | |
| 2004/0210404 A1 | 10/2004 | Gysling et al. | |
| 2004/0226386 A1 | 11/2004 | Croteau et al. | |
| 2004/0231431 A1 | 11/2004 | Bailey et al. | |
| 2004/0255695 A1 | 12/2004 | Gysling et al. | |
| 2005/0000289 A1 | 1/2005 | Gysling et al. | |
| 2005/0005711 A1 | 1/2005 | Gysling et al. | |
| 2005/0005712 A1 | 1/2005 | Gysling et al. | |
| 2005/0005713 A1 | 1/2005 | Winston et al. | |
| 2005/0005912 A1 | 1/2005 | Gysling et al. | |
| 2005/0011258 A1 | 1/2005 | Gysling et al. | |
| 2005/0011283 A1 | 1/2005 | Gysling et al. | |
| 2005/0011284 A1 | 1/2005 | Gysling et al. | |
| 2005/0012935 A1 | 1/2005 | Kersey | |
| 2005/0033545 A1 | 2/2005 | Gysling | |
| 2005/0039520 A1 | 2/2005 | Davis et al. | |
| 2005/0044929 A1 | 3/2005 | Gysling et al. | |
| 2005/0044966 A1 | 3/2005 | Gysling et al. | |
| 2005/0050956 A1 | 3/2005 | Gysling et al. | |
| 2005/0061060 A1 | 3/2005 | Banach et al. | |
| 2005/0072216 A1 | 4/2005 | Engel | |
| 2005/0125166 A1 | 6/2005 | Loose et al. | |
| 2005/0125170 A1 | 6/2005 | Gysling et al. | |
| 2005/0171710 A1 | 8/2005 | Gysling et al. | |

FOREIGN PATENT DOCUMENTS

| | | |
|---|---|---|
| EP | 1186868 | 3/2002 |
| WO | WO 93/14382 | 7/1993 |
| WO | WO 99/67629 | 12/1999 |
| WO | WO 00/00793 | 1/2000 |
| WO | WO 00/46583 | 8/2000 |
| WO | WO 01/02810 | 1/2001 |
| WO | WO 02/50511 | 6/2002 |
| WO | WO 2004/063741 | 7/2004 |

OTHER PUBLICATIONS

D.O. Thompson and D.E. Chimenti, non-intrusive, ultrasonic measurement of fluid composition, 1998, p. 1-8.*

Harshal B. Nemade, IEEE transactions on instrumentation and measurement, vol. 47, No. 1, Feb. 1998, p. 265-269.* http://en.wikipedia.org/wiki/Convection, p. 1-5.*

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attentuation of Acoustic Waves in Suspensions" by R.L. Gibson, Jr. and M.N. Toksoz, 1989.

Piezo Film Sensors Technical Manual—Provided by Measurement Specialties, Inc., Apr. 1999 p. 1-86.

Sonar-Based Volumetric Flow Meter For Pulp and Paper Applications—Daniel L. Gysling & Douglas H. Loose—Dec. 13, 2003.

Sonar-Based Volumetric Flow Meter for Chemical and Petrochemical Applications—Daniel L. Gysling & Douglas H. Loose—Feb. 14, 2003, p. 1-5.

New Flowmeter Principle—By Walt Boyes—Flow Control Magazine—Oct. 2003 Issue, p. 75.

Sonar Gets into the Flow—Daniel L. Gysling and Douglas H. Loose—Modern Process—Jan. 2004, p. 14-16.

"Acoustic Considerations Effecting the Design of Demodulators for the Ultrasonic Correlation Flow Meter" by: J.S. Battye, Sensors and Actuators A 88 (2001) pp. 29-40.

"Flow Velocity Measurement using Spatial Filter" by: Yoshio Kurita, Takaharu Matsumoto and Yukitake Shibata—Nov. 1979—pp. 239-244.

Piezo Film Sensors Technical Manual—Measurement Specialties Inc.—Sensor Products Division Apr. 2, 1999.

"Viscous Attentuation of Acoustic Waves in Suspensions" by R.L. Gibson, Jr. and M.N. Toksoz, May 1989, pp. 1925-1934.

Sonar-Based Volumetric Flow Meter For Pulp and Paper Applications—Daniel L. Gysling & Douglas H. Loose—Dec. 13, 2003, p. 1-5.

Sonar-Based Volumetric Flow Meter for Chemical and Petrochemical Applications—Daniel L. Gysling & Douglas H. Loose—Feb. 14, 2003, p. 1-8.

New Flowmeter Principle—By Walt Boyes—Flow Control Magazine—Oct. 2003 Issue.

* cited by examiner

APPARATUS AND METHOD USING AN ARRAY OF ULTRASONIC SENSORS FOR DETERMINING THE VELOCITY OF A FLUID WITHIN A PIPE

CROSS-REFERENCE TO RELATED PATENT APPLICATIONS

The present application claims the benefit of U.S. Provisional Patent Application, Ser. No. 60/439,715 filed Jan. 13, 2003, U.S. Provisional Patent Application, Ser. No. 60/524, 066 filed Nov. 21, 2003, U.S. Provisional Patent Application, Ser. No. 60/531,065 filed Dec. 19, 2003, U.S. Provisional Patent Application, Ser. No. 60/447,498 filed Feb. 14, 2003, and U.S. Provisional Patent Application, Ser. No. 60/440,014 filed Jan. 14, 2003, which are all incorporated herein by reference.

FIELD OF THE INVENTION

The present invention pertains to the field of processing ultrasonic signals such as in the field of sonar, and more particularly to the field of measurements of the velocity of a fluid when the direction of fluid flow is known, such as when the fluid flow is confined to a pipe.

BACKGROUND OF THE INVENTION

Currently, there are three classes of flow meters that utilize ultrasonic transducers, which include transit time ultrasonic flow meters (TTUF), doppler ultrasonic flow meters (DUF), and cross correlation ultrasonic flow meters (CCUF).

CCUF's measure the time required for ultrasonic beams to transit across a flow path at two, axially displaced locations along a pipe. Within this measurement principle, variations in transit time are assumed to correlate with properties that convect with the flow, such as vortical structure, inhomogenities in flow composition, temperature variations to name a few.

CCUF's utilize high frequency acoustic signals, i.e. ultrasonics, to measure much lower frequency, time varying properties of structures in the flow. Like all other cross correlation based flow meters, the physical disturbances which cause the transit time variations should retain some level of coherence over the distance between the two sensors.

Cross correlation ultrasonic flow meters have been around since the early 1960's. CCUF's are typically much more robust to variations in fluid composition than the other ultrasonic-based flow measurement approaches such as transit time and Doppler based methods.

Although CCFU's are operationally more robust than other ultrasonic interpretation techniques, they suffer from drawbacks attributed to most cross correlation flow meters, i.e., they are have slow update rates and relatively inaccurate.

Transit time, defined as the time required for an ultrasonic beam to propagate a given distance, can be measured using a radially aligned ultrasonic transmitter and receiver. For a homogenous fluid with a no transverse velocity components flowing in an infinitely rigid tube, the transit time is given by the following relation:

$$t = D/A_{mix}$$

t is the transit time, D is the diameter of the pipe, and Amix is the speed of sound propagating through the fluid.

In such a flow, variation in transit time is analogous to a variation in sound speed of the fluid. In real fluids however, there are many mechanisms, which could cause small variations in transit time which remain spatially coherent for several pipe diameters. For single phase flows, variations in the transverse velocity component will cause variations in transit time. Variations in the thermophysical properties of a fluid such as temperature or composition will also cause variations. Many of these effects convect with the flow. Thus influence of transverse velocity of the fluid associated with coherent vortical structures on the transit time enables transit time based measurements to be suitable for cross correlation flow measurement for flows with uniform composition properties. The combination of sensitivity to velocity field perturbation and to composition changes make transit time measurement well suited for both single and multiphase applications.

Despite CCUFs functioning over a wide range of flow composition, standard transit time ultrasonic flow meters (TTUF) are more widely used. TTUF tend to require relatively well behaved fluids (i.e. single phase fluids) and well-defined coupling between the transducer and the fluid itself. TTUFs rely on transmitting and receive ultrasonic signals that have some component of their propagation in line with the flow. While this requirement further does not pose a significant issue for in-line, wetted transducer TTUFs, it does pose a challenge for clamp-on devices by introducing the ratio of sound speed in the pipe to the fluid as an important operating parameter. The influence of this parameter leads to reliability and accuracy problems with clamp-on TTUFs.

CCFUs, utilize ultrasonic transducers to launch and detect ultrasonic waves propagating normal to the flow path. Refraction of ultrasonic waves at the pipe/fluid interface is not an issue and the ratio between sound speed of pipe and the fluid does not direct effect operability.

The primary issue with CCFUs is that they are slow and inaccurate. CCFUs rely on cross correlation of two measurements utilizing time domain cross correlation.

A flow meter embodying the present invention utilizes an array of ultrasonic transmitters and receivers to observe a measured property of a flow through a pipe, i.e. transit time and/or amplitude, at respective axial location, combined with array beam-forming techniques to create a new type of sonar-based, ultrasonic flow meter to overcome drawbacks of current ultrasonic meters Using sonar-based array processing methods to interpret the output of multiple transit time transmitting and receiving sensor pairs would result in enhanced performance over the current CCFUs. The enhanced performance would include better accuracy, faster update rate and more robust operation.

SUMMARY OF THE INVENTION

Objects of the present invention include providing an apparatus having an array of ultrasonic sensor units for measuring the velocity of a fluid flowing within a pipe wherein beam forming techniques are used to provide a robust flow meter.

In accordance with the present invention, a method for measuring the flow velocity of a fluid flowing through an elongated body substantially along the longest axis of the elongated body is provided. The method comprises providing an array of at least two ultrasonic sensor units disposed at predetermined locations along the elongated body. Each sensor unit includes an ultrasonic transmitter and an ultrasonic receiver. Each sensor unit provides a respective signal indicative of a parameter of an ultrasonic signal propagating between each respective ultrasonic transmitter and ultrasonic receiver. The method further includes processing the transit time signals to define a convective ridge in the k-ω plane; and determining the slope of at least a portion of the convective ridge to determine the flow velocity of the fluid.

In accordance with another embodiment of the present invention, an apparatus for measuring the flow velocity of a fluid flowing through an elongated body substantially along the longest axis of the elongated body is provided. The apparatus includes an array of at least two ultrasonic sensor units disposed at predetermined locations along the elongated body. Each sensor unit includes an ultrasonic transmitter and an ultrasonic receiver. Each sensor unit provides a respective signal indicative of a parameter of an ultrasonic signal propagating between each respective ultrasonic transmitter and ultrasonic receiver. A processor defines a convective ridge in the k-ω plane in response to the ultrasonic signals, and determines the slope of at least a portion of the convective ridge to determine the flow velocity of the fluid.

In accordance with the another embodiment of the present invention, an apparatus for measuring the flow velocity of a fluid flowing through an elongated body substantially along the longest axis of the elongated body is provided. The apparatus includes an array of at least two ultrasonic sensor units disposed at predetermined locations along the elongated body. Each sensor unit includes an ultrasonic transmitter and an ultrasonic receiver. Each sensor unit provides a respective signal indicative of a parameter of an ultrasonic signal propagating between each respective ultrasonic transmitter and ultrasonic receiver. A means is provided for processing the ultrasonic signals to define a convective ridge in the k-ω plane. A means is provided for determining the slope of at least a portion of the convective ridge to determine the flow velocity of the fluid.

The foregoing and other objects, features and advantages of the present invention will become more apparent in light of the following detailed description of exemplary embodiments thereof.

BRIEF DESCRIPTION OF THE DRAWINGS

The above and other objects, features and advantages of the invention will become apparent from a consideration of the subsequent detailed description presented in connection with accompanying drawings, in which.

BEST MODE FOR CARRYING OUT THE INVENTION

Figure 1:
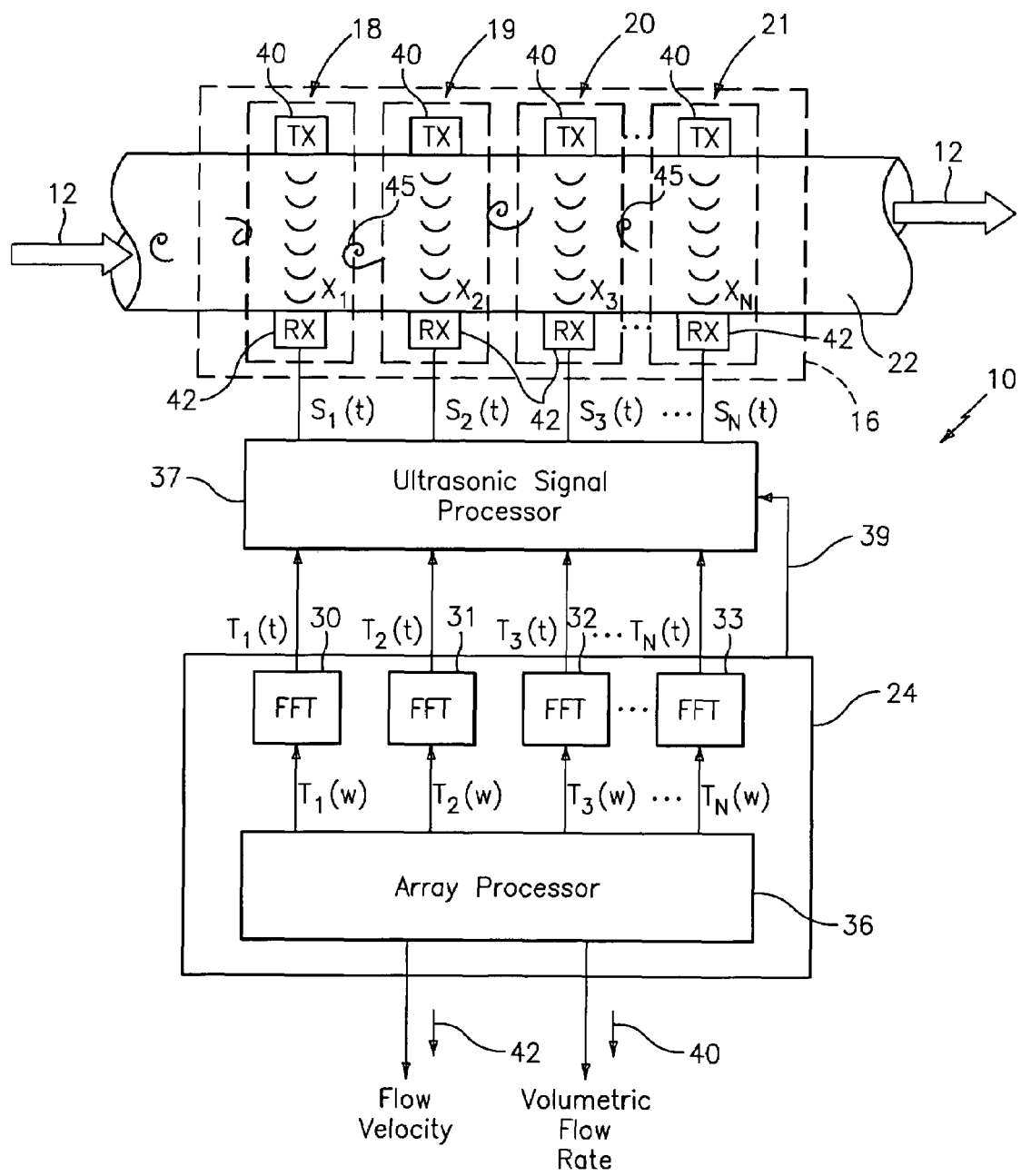
FIG. 1 is a block diagram of a flow meter having an array of ultrasonic sensor units disposed axially along a pipe for measuring the volumetric flow of the fluid flowing in the pipe, in accordance with the present invention.

Referring to FIG. 1, a flow meter, generally shown as 10, is provided to measure the velocity and/or volumetric flow rate of a single phase fluid 12 (e.g., gas, liquid or liquid/liquid mixture) and/or a multi-phase mixture 12 (e.g., process flow) flowing through a pipe. The multi-phase mixture may be a two-phase liquid/gas mixture, a solid/gas mixture or a solid/liquid mixture, gas entrained liquid or a three-phase mixture.

The flow meter 10 includes a sensing device 16 comprising an array of ultrasonic sensor units 18-21. Each sensor unit comprises a pair of ultrasonic sensors 40,42, one of which functions as a transmitter (Tx) 40 and the other as a receiver (Rx) 42. The sensor units 18-21 are spaced axially along the outer surface 22 of a pipe 14 having a process flow 12 propagating therein. The pair of sensors 40,42 is diametrically disposed on the pipe at predetermined locations along the pipe to provide a through transmission configuration, such that the sensors transmit and receive an ultrasonic signal that propagates through the fluid substantially orthogonal to the direction of the flow of the fluid within the pipe.

As shown in FIG. 1, each pair of ultrasonic sensors 40,42 measures a transit time (i.e., time of flight (TOF), or phase modulation) of an ultrasonic signal propagating through the fluid 12 from the transmitting sensor 40 to the receiving sensor 42. The transit time measurement or variation is indicative of a coherent properties that convect with the flow within the pipe (e.g., vortical disturbances, inhomogenieties within the flow, temperature variations, bubbles, particles, pressure disturbances), which are indicative of the velocity of the process flow 12. The ultrasonic sensors may operate at any frequency, however, it has be found that the higher frequency sensors are more suitable for single phase fluids while lower frequency sensors are more suitable for multiphase fluids. The optimum frequency of the ultrasonic sensor is dependent on the size or type of particle or substance propagating with the flow 12. For instance, the larger the air bubbles in an aerated fluid the lower the desirable frequency of the ultrasonic signal. Examples of frequency used for a flow meter embodying the present invention are 1 MHz and 5 MHz. The ultrasonic sensors may also provide a pulsed, chirped or continuous signal through the fluid flow 12. An example of the sensors 40,42 that may be used are Model no. 113-241-591, manufactured by Krautkramer.

An ultrasonic signal processor 37 fires the sensors 40 in response to a firing signal 39 from the transmitter 24 and receives the ultrasonic output signals $S_1(t)$-$S_N(t)$ from the sensors 42. The signal processor 37 processes the data from each of the sensor units 18-21 to provide an analog or digital output signal $T_1(t)$-$T_N(t)$ indicative of the time of flight or transit time of the ultrasonic signal through the fluid. The signal processor 37 may also provide an output signal indicative of the amplitude (or attenuation) of the ultrasonic signals. One such signal processor is model no. USPC 2100 manufactured by Krautkramer Ultrasonic Systems. Measuring the amplitude of ultrasonic signal is particularly useful and works best for measuring the velocity of a fluid that includes a substance in the flow (e.g., multiphase fluid or slurry).

The output signals ($T_1(t)$-$T_N(t)$) of the ultrasonic signal processor 37 are provided to the processor 24, which processes the transit time measurement data to determine the volumetric flow rate. The transit time or time of flight measurement is defined by the time it takes for an ultrasonic signal to propagate from the transmitting sensor 40 to the respective receiving sensor 42 through the pipe wall and the fluid 12. The effect of the vortical disturbances (and/or other inhomogenities within the fluid) on the transit time of the ultrasonic signal is to delay or speed up the transit time. Therefore, each sensing unit 18-21 provides a respective output signal $T_1(t)$-$T_N(t)$ indicative of the variations in the transit time of the ultrasonic signals propagating orthogonal to the direction of the fluid 12. The measurement is derived by interpreting the convecting coherent property and/or characteristic within the process piping using at least two sensor units 18,19. The ultrasonic sensors 18-21 may be "wetted" or clamped onto the outer surface 22 of the pipe 14 (e.g. contact or non-contact sensor).

In one example, the flow meter 10 measures the volumetric flow rate by determining the velocity of vortical disturbances or "eddies" 45 (see FIG. 2) propagating with the flow 12 using the array of ultrasonic sensors 18-21. The flow meter 10 measures the velocities associated with unsteady flow fields created by vortical disturbances or "eddies" 45 and other inhomogenities to determine the velocity of the flow 12. The ultrasonic sensor units 18-21 measure the transmit time $T_1(t)$-$T_N(t)$ of the respective ultrasonic signals between each respective pair of sensors 40,42, which vary due to the vortical disturbances as these disturbances convect within the flow 12 through the pipe 14 in a known manner. Therefore, the velocity of these vortical disturbances is related to the velocity of the flow 12 and hence the volumetric flow rate may be determined, as will be described in greater detail hereinafter. The volumetric flow is determined by multiplying the velocity of the fluid by the cross-sectional area of the pipe.

To measure volumetric flow, the flow meter 10 characterizes the velocity at which coherent vortical structures convect past the axial array of sensor units 18-21. Coherent structures 45 are an inherent feature of turbulent boundary layers present in all turbulent flows. Unlike conventional vortex shedding meters, no internal geometry is required to generate these structures.

The overwhelming majority of industrial process flows 12 involve turbulent flow. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar based array processing flow metering technology, understanding the time-averaged velocity profile in turbulent flow 12 provides a means to interpret the relationship between speed at which coherent structures 45 convect and the volumetrically averaged flow rate.

Turbulent pipe flows 12 are highly complex flows. Predicting the details of any turbulent flow is problematic, however, much is known regarding the statistical properties of the flow. For instance, turbulent flows contain self-generating, coherent vortical structures often termed "turbulent eddies". The maximum length scale of these eddies is set by the diameter of the pipe 14. These structures remain coherent for several pipe diameters downstream, eventually breaking down into progressively smaller eddies until the energy is dissipated by viscous effects.

Experimental investigations have established that eddies generated within turbulent boundary layers convect at roughly 80% of maximum flow velocity. For pipe flows, this implies that turbulent eddies will convect at approximately the volumetrically averaged flow velocity within the pipe 14. The precise relationship between the convection speed of turbulent eddies and the flow rate for each class of meters can be calibrated empirically as described below.

Figure 2:
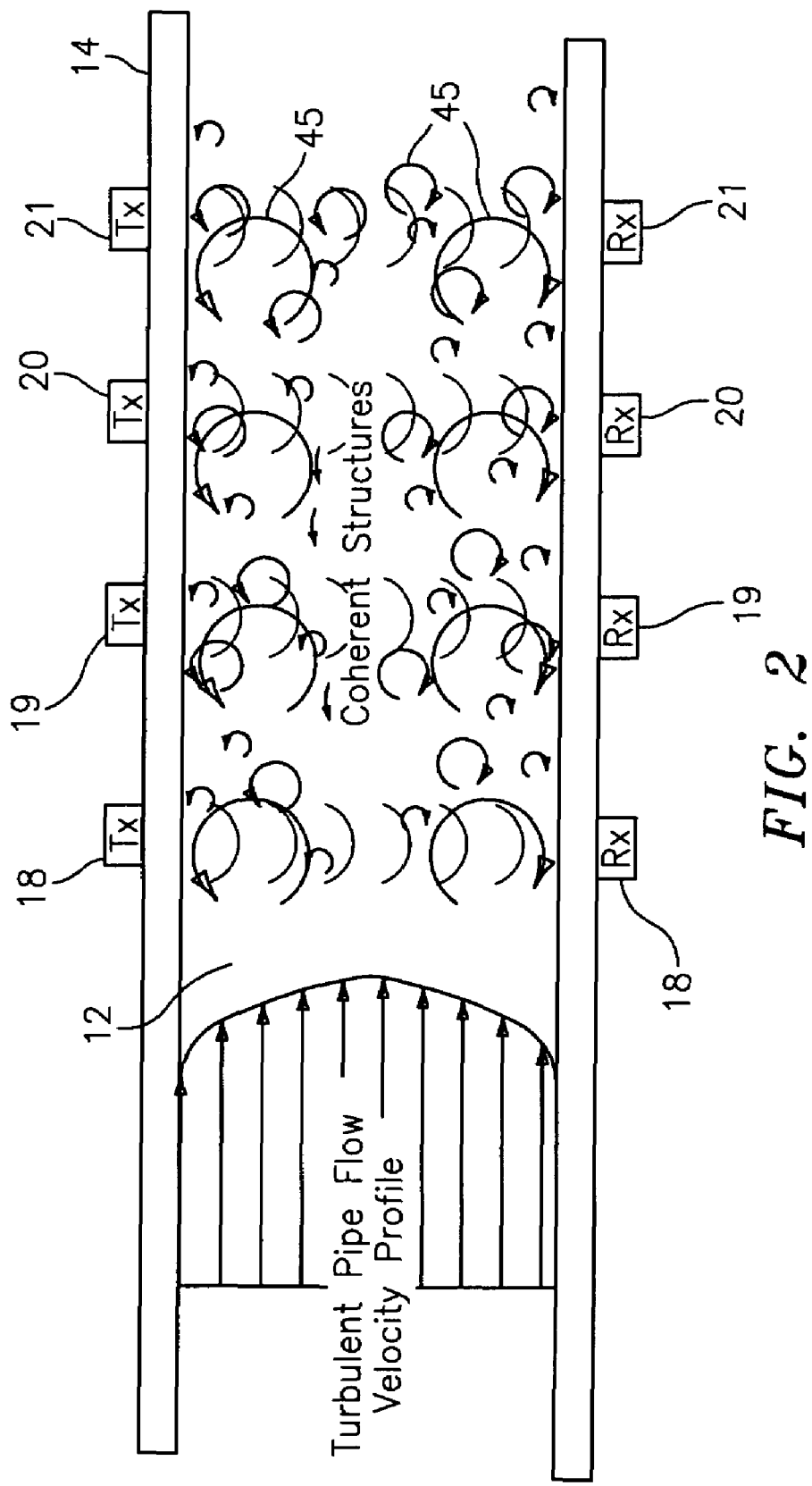
FIG. 2 is a cross-sectional view of a pipe having a turbulent pipe flowing having coherent structures therein, in accordance with the present invention.

FIG. 2 illustrates the relevant flow features of turbulent pipe flow 12 along with an axial array of ultrasonic sensor units 18-21, each sensor unit having a transmitter unit 40 and a receiver unit 42. As shown, the time-averaged axial velocity is a function of radial position, from zero at the wall to a maximum at the centerline of the pipe. The flow 12 near the wall is characterized by steep velocity gradients and transitions to relatively uniform core flow near the center of the pipe 14. Vortical structures, often termed turbulent eddies, are superimposed over time averaged velocity profile. These coherent structures contain temporally and spatially random fluctuations with magnitudes typically less than 10% percent of the mean flow velocity and are carried along with the mean flow. Experimental investigations have established that eddies generated within turbulent boundary layers remain coherent for several pipe diameters and convect at roughly 80% of maximum flow velocity (Schlichting, 1979).

From a volumetric flow measurement perspective, the volumetrically averaged flow velocity is of interest. The volumetrically averaged flow velocity, defined as the total volumetric flow rate, Q, divided by the cross sectional area of the conduit, A, is a useful, but arbitrarily defined property of the flow. In fact, given the velocity profile within the pipe, little flow is actually moving at this speed. The precise relationship between the convection speed of turbulent eddies and the flow rate is determined experimentally through calibration for each.

The Reynolds number (Re), based on pipe diameter (D), characterizes many of the engineering properties of the flow. The Reynolds number is a non-dimensional ratio representing the relative importance of inertial forces to viscous forces within a flow:

$$Re = \frac{\text{inertial}}{\text{viscous}} \text{ forces} = \frac{\rho u \frac{\partial u}{\partial x}}{\mu \frac{\partial^2 u}{\partial y^2}} = \frac{UD}{\nu}$$

Where $\rho$ is the fluid density, $\mu$ is the dynamic viscosity, U is the volumetrically averaged flow velocity and $\nu$ ($=\mu/\rho$) is the kinematic viscosity.

The critical Reynolds number for pipe flows, above which flows are considered turbulent, is ~2300. In addition to demarcating a boundary between laminar and turbulent flow regimes, the Reynolds number is a similarity parameter for pipe flows, i.e. flows in geometrically dissimilar pipes with the same Reynolds number are dynamically similar (Schlichting p.12).

As shown in FIG. 1, the flow meter 10 embodying the present invention has an array of at least two ultrasonic sensor units 18-19, located at locations $x_1, x_2$ axially along the pipe 14. One will appreciate that the sensor array may include three or more ultrasonic sensor units as depicted by ultrasonic sensor units 20, 21 at locations $x_3, x_N$, respectively. The present invention contemplates that the array 16 may comprise any number of sensing units 18-21 or greater, which includes arrays that may have between 2 and 16 sensor units. The ultrasonic sensors provide transit time-varying signals $T_1(t), T_2(t), T_3(t), T_N(t)$ to a signal processor 24 to known Fast Fourier Transform (FFT) logics 30-33, respectively. The FFT logics 30-33 calculate the Fourier transform of the time-based input signals $T_1(t)$-$T_N(t)$ and provide complex frequency domain (or frequency based) signals $T_1(\omega), T_2(\omega), T_3(\omega), T_N(\omega)$ indicative of the frequency content of the input signals. Instead of FFT's, any other technique for obtaining the frequency domain characteristics of the signals $T_1(t)$-$T_N(t)$, may be used.

The frequency signals $T_{1(\omega)-TN}(\omega)$ are fed to an array processor 36, which provides a flow signal 40 indicative of the volumetric flow rate of the process flow 12 and a velocity signal 42 indicative of the velocity of the process flow.

One technique of determining the convection velocity of the vortical disturbances within the process flow 12 is by characterizing the convective ridge of the vortical disturbances using an array of unsteady ultrasonic sensors or other beam forming techniques, similar to that shown in U.S. patent application Ser. No. 09/729,994, filed Dec. 4, 2000, entitled "Method and Apparatus for Determining the Flow Velocity Within a Pipe", which is incorporated herein by reference. This technique of determining the convection velocity of the vortical disturbances will be described in greater detail hereinafter.

The flow metering methodology uses the convection velocity of coherent structure with turbulent pipe flows 12 to determine the volumetric flow rate. The convection velocity of these eddies 45 is determined by applying arraying processing techniques to determine the speed at which the eddies convect past the axial ultrasonic sensor array of distributed along the pipe 14, similar to that used in the radar and sonar fields.

The array processing algorithms determine the speed of the eddies 45 by characterizing both the temporal and spatially frequency characteristics of the flow field. For a series of coherent eddies convecting past a fixed array of ultrasonic sensors units 18-21, the temporal and spatial frequency content of pressure fluctuations are related through the following relationship:

$$k = \frac{\omega}{U_{convect}}$$

Here k is the wave number or spatial frequency, defined as $k=2\pi/\lambda$ and has units of 1/length, $\omega$ is the temporal frequency in rad/sec, and $U_{convect}$ is the convection velocity. Thus, the temporal frequency, $\omega$, is linearly related to the spatial frequency, k, by the convection velocity.

In array processing, the spatial/temporal frequency content of time stationary sound fields are often displayed using "k-$\omega$ plots". K-$\omega$ plots are essentially three-dimensional power spectra in which the power of the field is decomposed into bins corresponding to specific spatial wave numbers and temporal frequencies. On a k-$\omega$ plot, the power associated with a pressure field convecting with the flow is distributed in regions, which satisfies the dispersion relationship developed above. This region is termed "the convective ridge" (Beranek, 1992) and the slope of this ridge on a k-$\omega$ plot indicates the convective velocity of the pressure field determine by measuring the variation in the TOF by each ultrasonic sensor unit 18-21. This suggests that the convective velocity of turbulent eddies, and hence flow rate within a pipe, can be determined by constructing a k-$\omega$ plot from the output of an array of sensor and identifying the slope of the convective ridge, as will described in greater detail hereinafter.

As described hereinbefore, the apparatus 10 of FIG. 1 is based on the observation that vortical disturbances within a moving fluid (and/or other characteristics of the fluid that convect with the flow, described hereinabove) vary the transit time of the ultrasonic signal, which can be sensed by ultrasonic sensors 40, 42, and that the vortical disturbances move at either the same velocity as the moving fluid, or at a velocity that can be correlated to the velocity of the moving fluid. The array processing can be performed by exploiting what is sometimes called the dispersion relationship associated with convective disturbances (i.e. $\omega=uk$, where $\omega$ is the angular frequency of the signal of the vortical disturbance, u is the velocity of the disturbance, and k is the wavenumber of the signal). Convective disturbances in a flowing fluid can be viewed as disturbances that are fixed to the fluid. These disturbances have a spatial variation associated with them. Since the disturbance can be viewed as affixed to the fluid particles, the spatial variations result in temporal variations when sensed by stationary sensors. The spatial wavelength of the disturbances that move with the fluid is thereby linked to the temporal variations observed by the stationary sensors. The present invention relies on utilizing array processing techniques to identify this relationship and thereby determine the convection velocity of the fluid.

Figure 3:
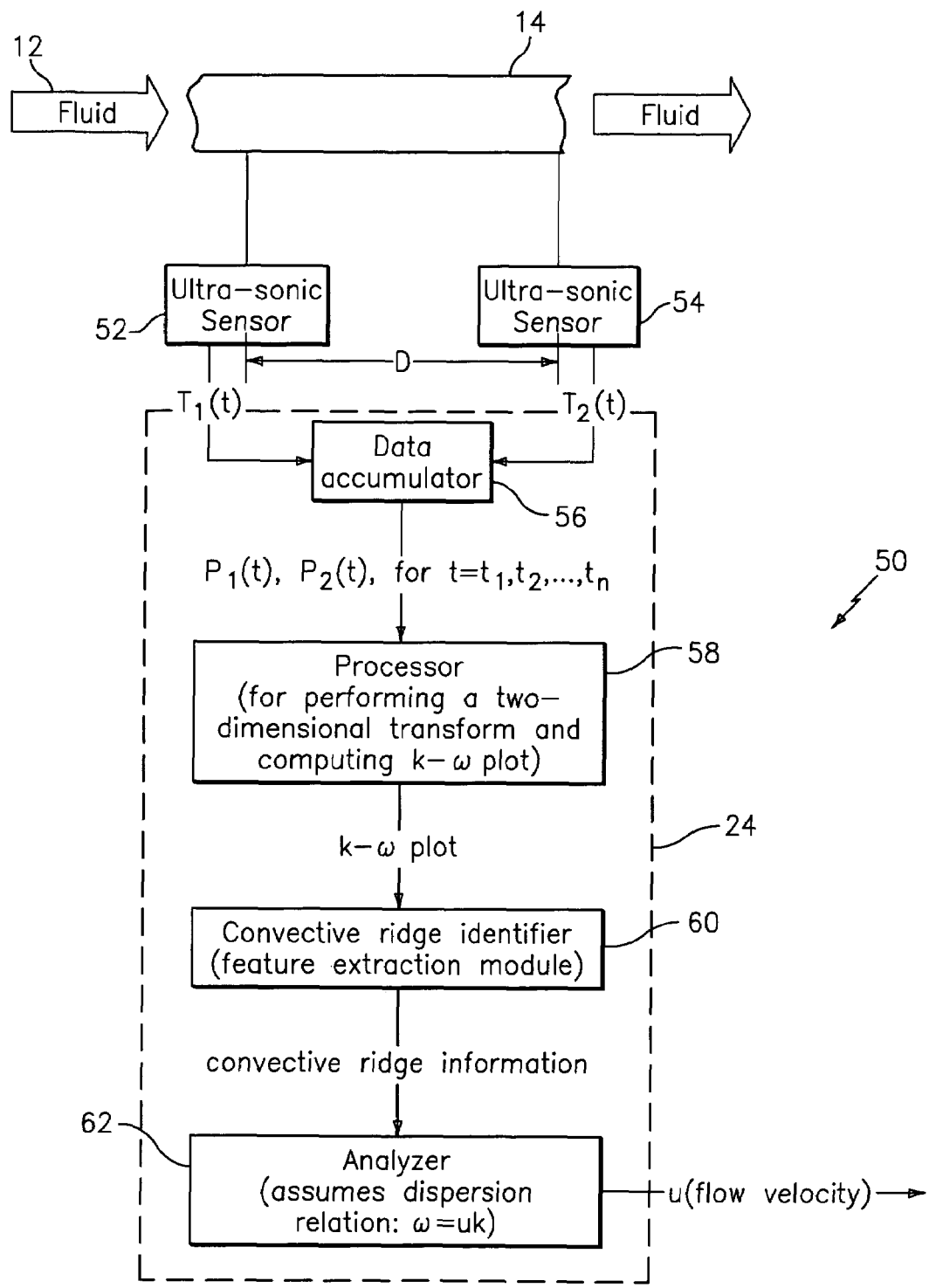
FIG. 3 is a process flow diagram/schematic view of a flow meter, in accordance with the present invention.

Referring now to FIG. 3, an apparatus 50, embodying the present invention, for determining a volumetric flow rate of a fluid 12 within a conduit (pipe) 14 is shown as including an array of ultrasonic sensor units 52, 54, each having a pair of sensors 40, 42 (transmitter and receiver, respectively), similar to that described hereinbefore, disposed axially along the pipe for sensing transit time of the ultrasonic signal propagating between the sensors 40,42 within the pipe at their respective locations. Each ultrasonic sensor unit 18-21 provides a signal indicating the transit time of an ultrasonic signal propagating through and orthogonal to the fluid flow, at the location of the sensor unit, at each instant in a series of sampling instants. A data accumulator 56 accumulates the signals T1 (t) and T2 (t) from the ultrasonic sensor units, and provides the data accumulated over a sampling interval to a processor 58, which performs a spatial-temporal (two-dimensional) transform of the sensor data, from the xt domain to the k-ω domain, and then calculates the power in the K-w plane, as represented by k-ω plot.

To calculate the power in the k-ω plane, as represent by a k-ω plot (see FIG. 4) of either the ultrasonic signals or the differenced ultrasonic signals, the processor 58 determine the wavelength and so the (spatial) wavenumber k, and also the (temporal) frequency and so the angular frequency ω, of various of the spectral components of the ultrasonic waves created by the vortical disturbances. There are numerous algorithms available in the public domain to perform the spatial/temporal decomposition of arrays of sensor units 52, 54.

Figure 4:
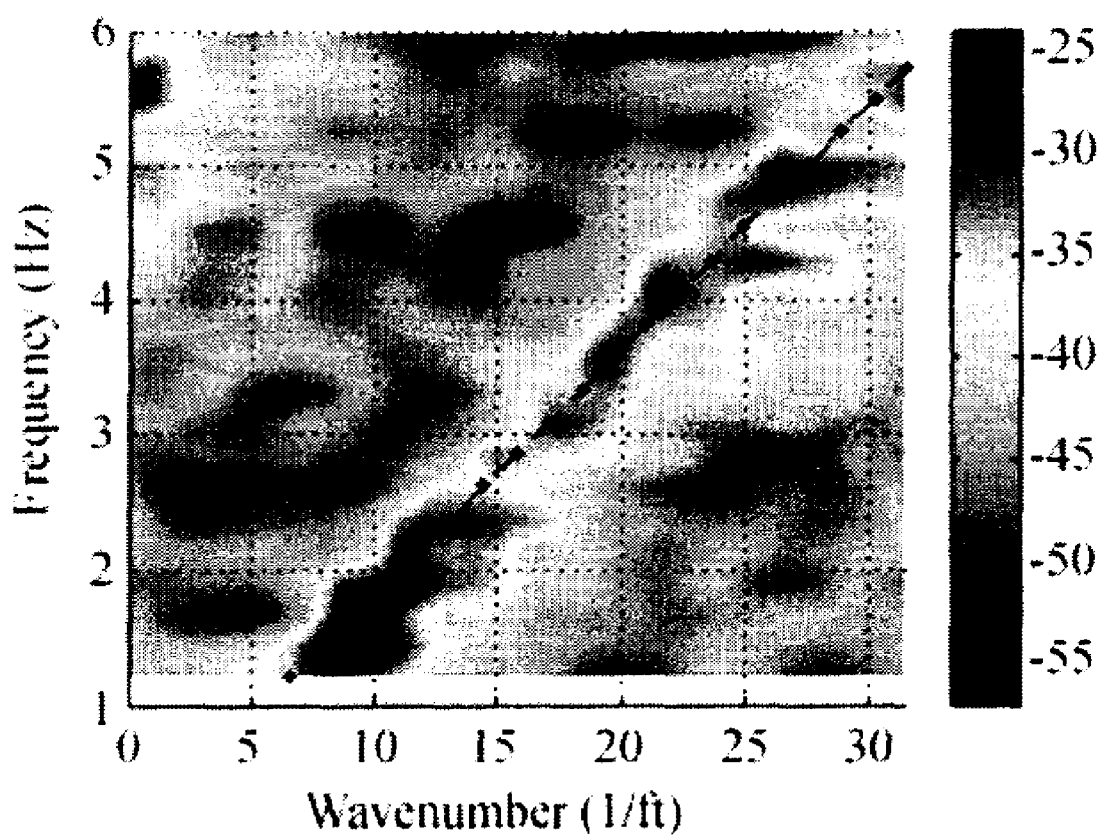
FIG. 4 is a k-ω plot constructed according to the present invention, showing a convective ridge, wherein the fluid flowing in the pipe is water.

In the case of suitable vortical disturbances being present, the power in the k-ω plane shown in a k-ω plot of FIG. 4 so determined will exhibit a structure that is called a convective ridge 61. The convective ridge represents the concentration of the disturbances that convect with the flow and is a mathematical manifestation of the relationship between the spatial variations and temporal variations described above. Such a plot will indicate a tendency for k-ω pairs to appear more or less along a line 63 with some slope, the slope indicating the flow velocity, as is described in more detail below. The power in the k-ω plane so determined is then provided to a convective ridge identifier 60, which uses one or another feature extraction method to determine the location and orientation (slope) of any convective ridge present in the k-ω plane. Finally, information including the convective ridge orientation (slope) is used by an analyzer 62 to determine the flow velocity.

The processor 58 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by vortical disturbances convecting with a flow are time stationary and have a coherence length long enough that it is practical to locate sensor units apart from each other and yet still be within the coherence length.

Convective disturbances, including convective vortical disturbances, have a dispersion relationship that can be approximated by the straight-line equation, $$k=\omega/u,$$

where u is the convection velocity (flow velocity). A plot of k-ω pairs obtained from a spectral analysis of sensor samples associated with convective disturbances portrayed so that the energy of the disturbance spectrally corresponding to pairings that might be described as a substantially straight ridge, a ridge that in turbulent boundary layer theory is called a convective ridge. What is being sensed are not discrete events of convective disturbance, but rather a continuum of possibly overlapping events forming a temporally stationary, essentially white process over the frequency range of interest. In other words, the convective disturbances, such as those generated by turbulent boundary layers, are distributed over a range of length scales and hence temporal frequencies.

Disturbances and other characteristics with these properties that convect with a fluid past the sensor array 52, 54 are transformed onto the convective ridge by the processor 58, the terminology ridge being appropriate because a k-ω plot indicates by one or another symbology the energy of k-ω pairs in the k-ω plane (i.e. the energy conveyed by the k-ω spectral component). Thus, identifying the convective ridge within the k-ω plane provides a means to determine the convective velocity. For flows within pipes, the convective velocity of the vortical disturbances is closely related to the average volumetric fluid velocity and therefore volumetric flow rate (flow velocity) within the pipe 14. While the apparatus 50 includes two sensor units 52, 54, the present invention contemplates more than two sensing units, such as 3 to 16 sensing units in an array, for example.

Once the power in the k-ω plane is determined, the convective ridge identifier 60 uses one or another feature extraction methodology to discern a convective ridge 61 and its orientation in the k-ω plane. In addition to automate techniques, a convective ridge can be located using even manual, visual inspection. In the preferred embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 60 provides information about the different trial convection velocities, information referred to generally as convective ridge information. The analyzer 62 examines the convective ridge information and, assuming the straight-line dispersion relation given by equation (1), determines the flow velocity and its uncertainty.

For turbulent boundary layers, the intensity of the turbulent fluctuations is roughly centered around $$\omega\delta^*\approx 1,$$

where $\delta^*$ is the displacement thickness of the boundary layer, a well known parameter in boundary layer analysis. For a three-inch pipe, assuming the displacement thickness of the boundary layer is 0.15 times the radius of the pipe, the center frequency in Hz of the turbulent energy is approximately ~10·u (with u in ft/sec). Thus, for flows in the 1-30 ft/sec regime, the convected energy resides at temporal frequencies below 10-300 Hz. For fully developed flow in a three-inch (typical) pipe, the spatial wave numbers of this peak activity is roughly constant with a wave number of 60 ft$^{-1}$, or, in terms of wavelengths, of roughly 0.1 ft. These estimates are used to design the array of sensor units 52, 54 so as to be suitably placed to be able to identify the convective ridge and thereby yield a measurement of the flow velocity.

In sensing both spatial and temporal characteristics of a wavelike phenomenon using an array of sensor units 52, 54, the spatial length scales and coherence lengths of the phenomenon constrain the length scale of the array. Thus, in the case of measuring the flow velocity by sensing vortical disturbances, sensors must be closely spaced and located within a limited axial region; for flow velocities of less than 30 ft/sec in a three-inch diameter pipe, the sensor units should usually be spaced less than 1" apart. The axial region is approximately 0.3 of the diameter of the pipe 14.

A particular embodiment of the present invention used an array of eight (8) disposed axially along a pipe 14. FIG. 4 shows a k-ω plot generated from the output of the eight (8) sensor units measuring water flowing through an 8" pipe. The ultrasonic sensors operated at a frequency of 5 MHz and spaced a 1.2 inches. The wave number (spatial characteristic) is plotted on the ordinate and the frequency (temporal characteristic) is plotted on the abscissa. The intensity of each k-ω pair is indicated using contours. Disturbances propagating from left to right (in the direction of the flow) map into the right half-plane.

The span of the array is bounded not only by coherence lengths of a vortical disturbance, but also by the need to avoid (or at least recognize) spatial aliasing, which is analogous to temporal aliasing. If a pair of sensor units 52, 54 spans a distance $\Delta x$, then the pair of sensor units cannot distinguish between disturbances with a wavelength equal to $2\Delta x$ and disturbances with a wavelength that is an integral multiple of $2\Delta x$. Thus, the minimum wavelength that can be resolved unambiguously by two sensors at a spacing of $\Delta x$ is given by, $$\lambda = 2\Delta x,$$

which corresponds to a maximum resolvable wave number given by, $$k = \frac{\pi}{\Delta x}$$

For the above-mentioned embodiment, the maximum resolvable wave number was $k=21$ ft$^{-1}$. For disturbances with spatial wavenumber higher than the Nyquist wavenumber, the information wraps back into the k-ω plane. Nevertheless, if properly interpreted, this aliased information can still provide useful information.

As mentioned above, although automated techniques can be used to identify a convective ridge and determine its orientation (slope), even a manual best fit of a straight line gives acceptable results. These automated methods can account for aliased data as well. For the above-mentioned embodiment for which a k-ω plot is shown in FIG. 4, the straight line 63 resulting from a manual straight line fit is indicated in FIG. 4. The straight line has a slope of $\Delta \omega / \Delta k = 1.142$ ft/sec (after converting the frequency δ used as the ordinate to the corresponding angular frequency ν by multiplying the frequency ν by $2\pi$), which, as explained above, is either equal to the flow velocity or is correlated to the flow velocity in a determinate way.

It should be noted that a convective ridge is only approximated by a straight line. In reality, vortical structures of varying length convect at slightly different speeds resulting in curvature in the convective ridge, curvature, which will be noticeable in a k-ω plot. However, the straight-line approximation is useful for extracting a meaningful estimate of the flow velocity, although not limited to a straight line approximation. Also, it should be emphasized that what is actually determined by the method of the present invention is the average convection velocity of vortical disturbances, and so represents an approximation to the average volumetric velocity within the pipe. The actual flow is complex and the correlation between measured convection velocity (of vortical disturbances) and average volumetric velocity may require calibration.

Figure 5:
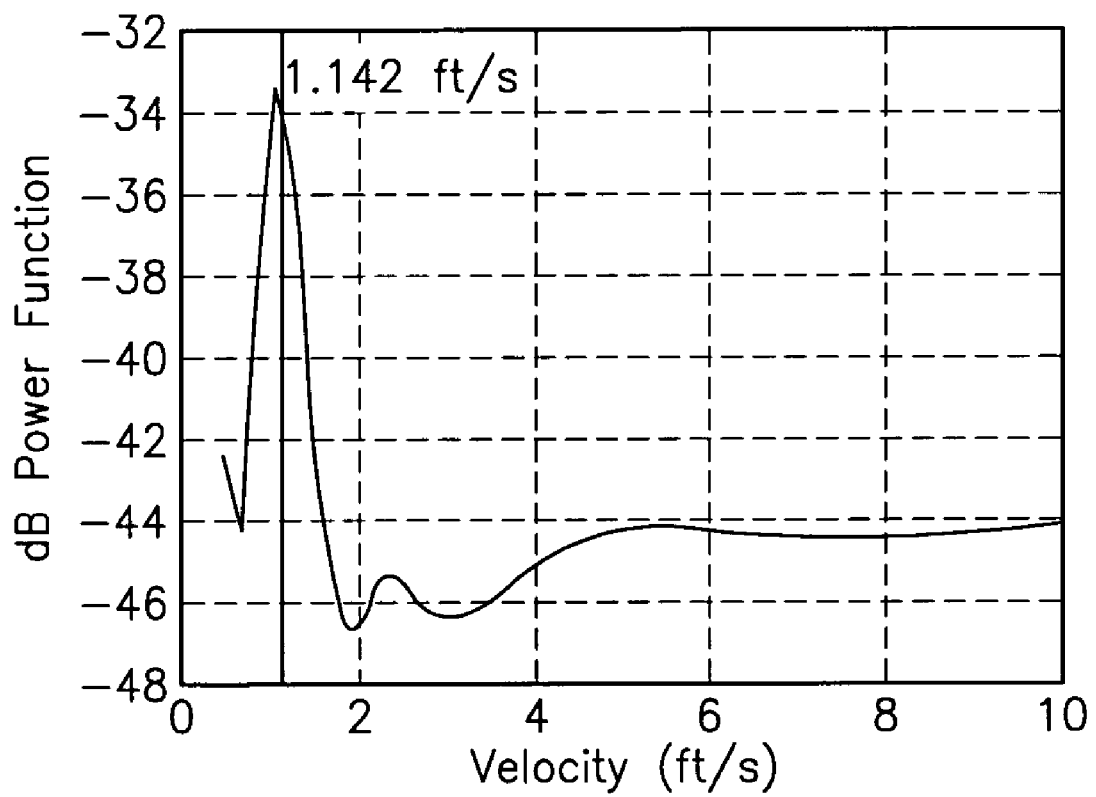
FIG. 5 is a plot of a dB power function versus velocity of the fluid of the k-ω plane for determining the slope having the greatest power which corresponds to the slope of the convective ridge in the k-ω plot of FIG. 4, in accordance with the present invention.

FIG. 5 shows a plot of the power in dB along a slope or convective ridge at a predetermined number of velocities. The results of analyzing each power associated at each velocity (or slope 61) in the k-ω plane is provided in FIG. 5. The slope of the convective ridge 61 is indicative of the velocity of the fluid flowing through the pipe 14. The convective ridge is determined, and therefore, the velocity, by determining the sum of the powers at each velocity (or slope) having the greatest power. The algorithm essentially sums the energy of k-ω pairs on a straight line associated with a trial convective velocity. The summation is performed for a range of trial velocities, and the convective ridge has an orientation that is the slope of the straight line 63 having the largest accumulated energy. In FIG. 5, the peak of the plot is indicative of the convective ridge and the velocity which is 1.142 ft/s. The peak of the plot make be determined using a number of peak detection algorithms, such as maximization algorithms and/or centroid algorithms. The present invention described hereinbefore is similar to that described in Provisional U.S. Patent Applications, Ser. Nos. 60/439,715, filed on Jan. 13, 2003 and 60/524,066, filed Nov. 12, 2003; U.S. Pat. No. 6,609,069 issued Aug. 19, 2003, U.S. patent application Ser. No. 10/007,736 filed Nov. 8, 2001, now U.S. Pat. No. 6,889,562; U.S. patent application Ser. No. 10/636,095, filed Aug. 7, 2003, now U.S. Pat. No. 7,181,955; U.S. patent application Ser. No. 10/712,818, filed Nov. 12, 2002; and U.S. patent application Ser. No. 10/712,833, filed Nov. 12, 2002; now abandoned, which are incorporated herein by reference.

Figure 6:
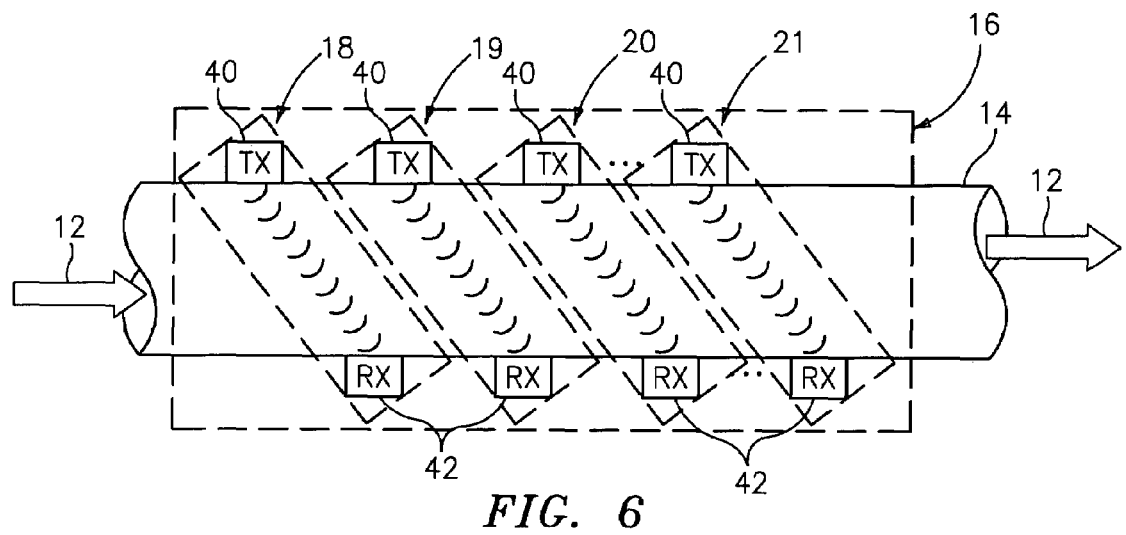
FIG. 6 is a block diagram of an alternative embodiment of a sensing device of a flow meter embodying the present invention similar to that shown in FIG. 1.

While each of the ultrasonic sensor units 18-21 of FIG. 1 and sensor units 52, 54 of FIG. 2,3 comprises a pair of ultrasonic sensors (transmitter and receiver) 40,42 are diametrically-opposed to provide through transmission, the present invention contemplates that one of the ultrasonic sensors 40,42 of each sensor unit 18-21 may be offset axially such that the ultrasonic signal from the transmitter sensor has an axial component in its propagation direction, as shown in FIG. 6.

Figure 7:
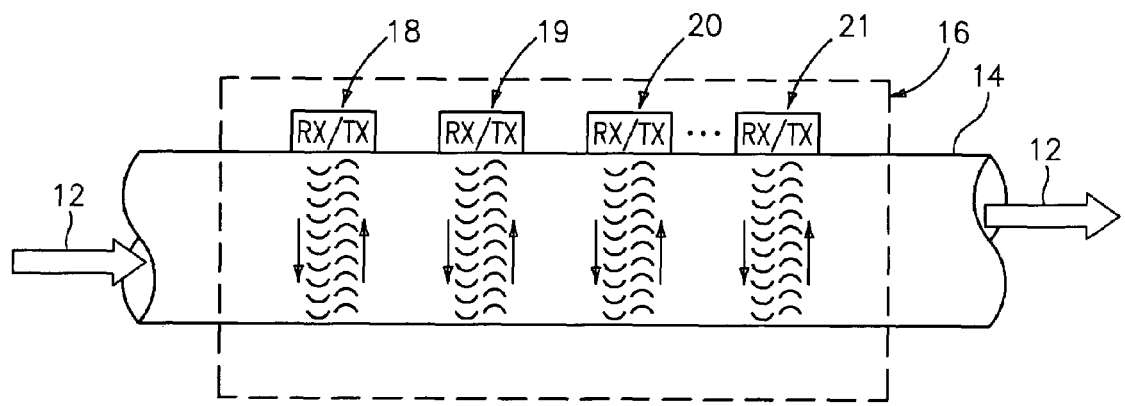
FIG. 7 is a block diagram of an alternative embodiment of a sensing device of a flow meter embodying the present invention similar to that shown in FIG. 1.

As shown in FIG. 7, the present invention also contemplates the sensor units 18-21 of the sensing device 16 may be configured in a pulse/echo configuration. In this embodiment, each sensing unit 18-21 comprises one ultrasonic sensor that transmits an ultrasonic signal through the pipe wall and fluid substantially orthogonal to the direction of flow and receives a reflection of the ultrasonic signal reflected back from the wall of the pipe to the ultrasonic sensor.

Figure 8:
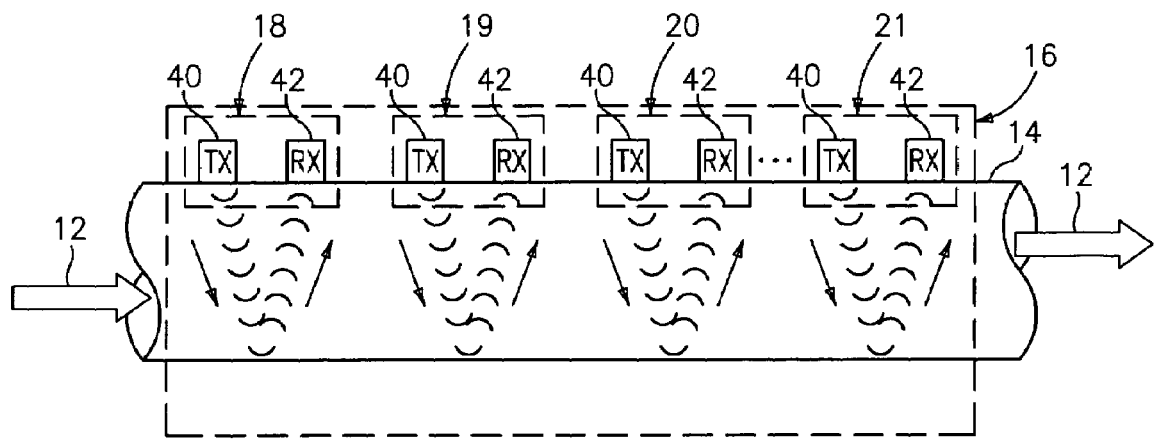
FIG. 8 is a block diagram of an alternative embodiment of a sensing device of a flow meter embodying the present invention similar to that shown in FIG. 1.

Referring to FIG. 8, the sensing device 16 may be configured to function in a pitch and catch configuration. In this embodiment, each sensor unit 18-19 comprises a pair of ultrasonic sensors (transmitter, receiver) 40, 42 disposed axially along the pipe disposed on the same side of the pipe at a predetermined distance apart. Each transmitter sensor 40 provides an ultrasonic signal a predetermined angle into the flow 12. The ultrasonic signal propagates through the fluid 12 and reflects of the inner surface of the pipe 14 and reflects the ultrasonic signal back through the fluid to the respective receiver sensor 42.

Figure 9:
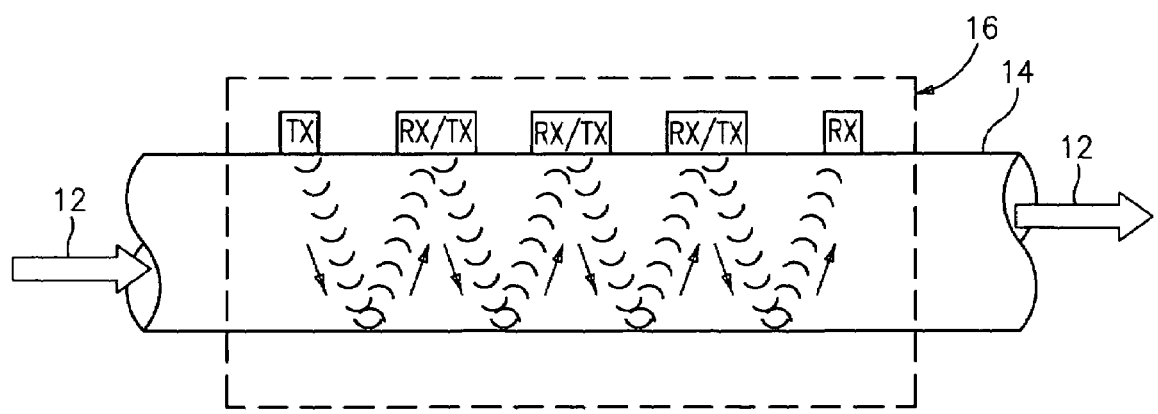
FIG. 9 is a block diagram of an alternative embodiment of a sensing device of a flow meter embodying the present invention similar to that shown in FIG. 1.

FIG. 9 shows another pitch and catch configuration for the sensing device 16 contemplated by the present invention. This configuration is similar to that shown in FIG. 8 except the sensors disposed between the end sensors function as both a transmitter and a receiver. This pitch and catch configuration reduces the number of sensors needed to operate.

Figure 10:
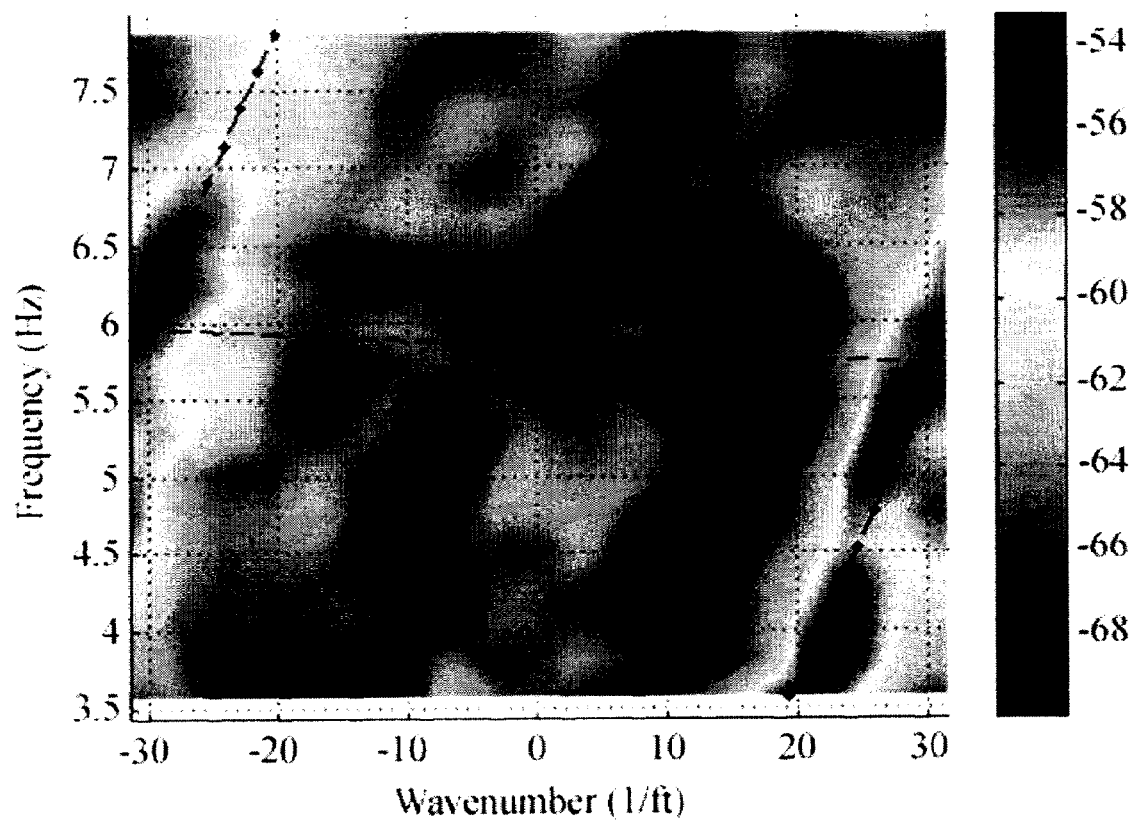
FIG. 10 is a k-ω plot constructed according to the present invention, showing a convective ridge, wherein the fluid flowing in a pipe is water at a low flow rate.
Figure 11:
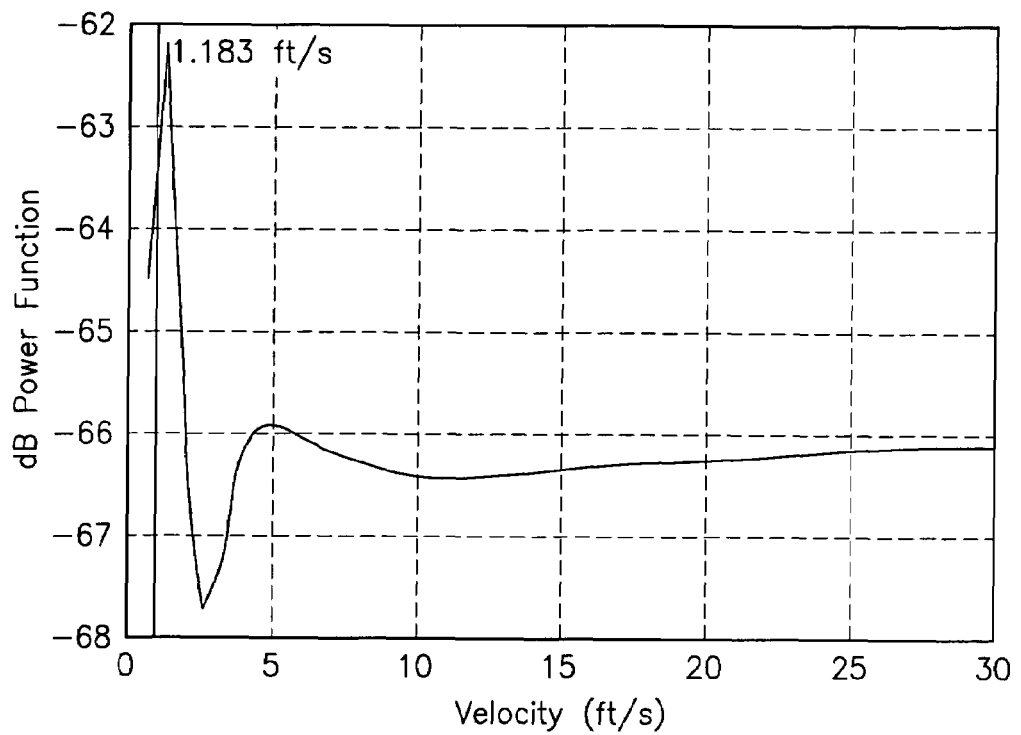
FIG. 11 is a plot of a dB power function versus velocity of the fluid of the k-ω plane for determining the slope having the greatest power, which corresponds to the slope of the convective ridge in the k-ω plot of FIG. 10, in accordance with the present invention.

FIG. 10 shows a k-ω plot determined from a flow meter embodying the present invention measuring the flow of pure water flowing within an 8 inch pipe. The flow meter, similar to that shown in FIG. 1, is configured as a through transmission configuration and is measuring time of flight of the ultrasonic signals through the fluid. The sensing device comprises eight (8) sensing units 18-21 spaced axially 1.2 inches apart. The sensors 40,42 include 5 MHz transducers. FIG. 11 illustrates the dB power function of the k-ω plot or plane shown in FIG. 10, which shows a flow rate of 1.183 ft/sec.

Figure 12:
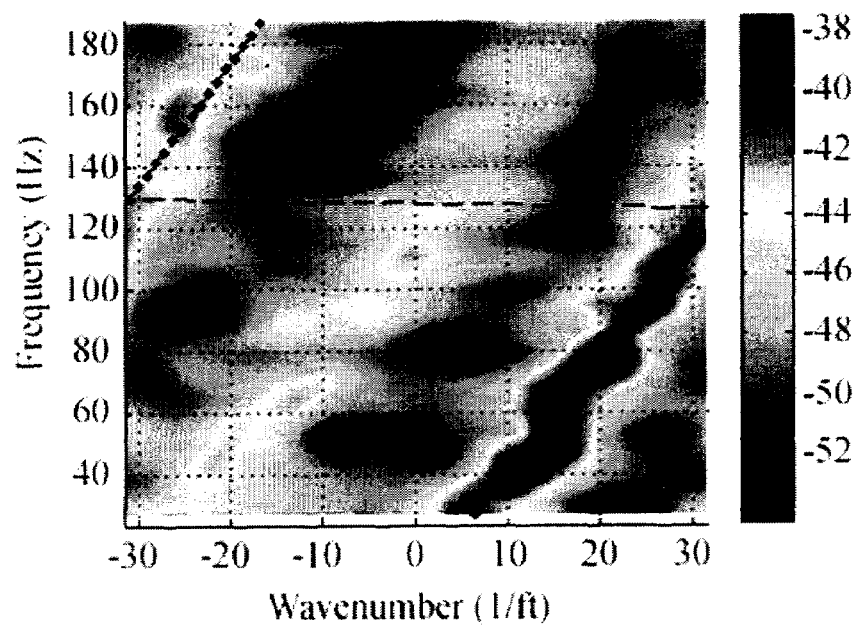
FIG. 12 is a k-ω plot constructed according to the present invention, showing a convective ridge, wherein the fluid flowing in a pipe is water having entrained air.
Figure 13:
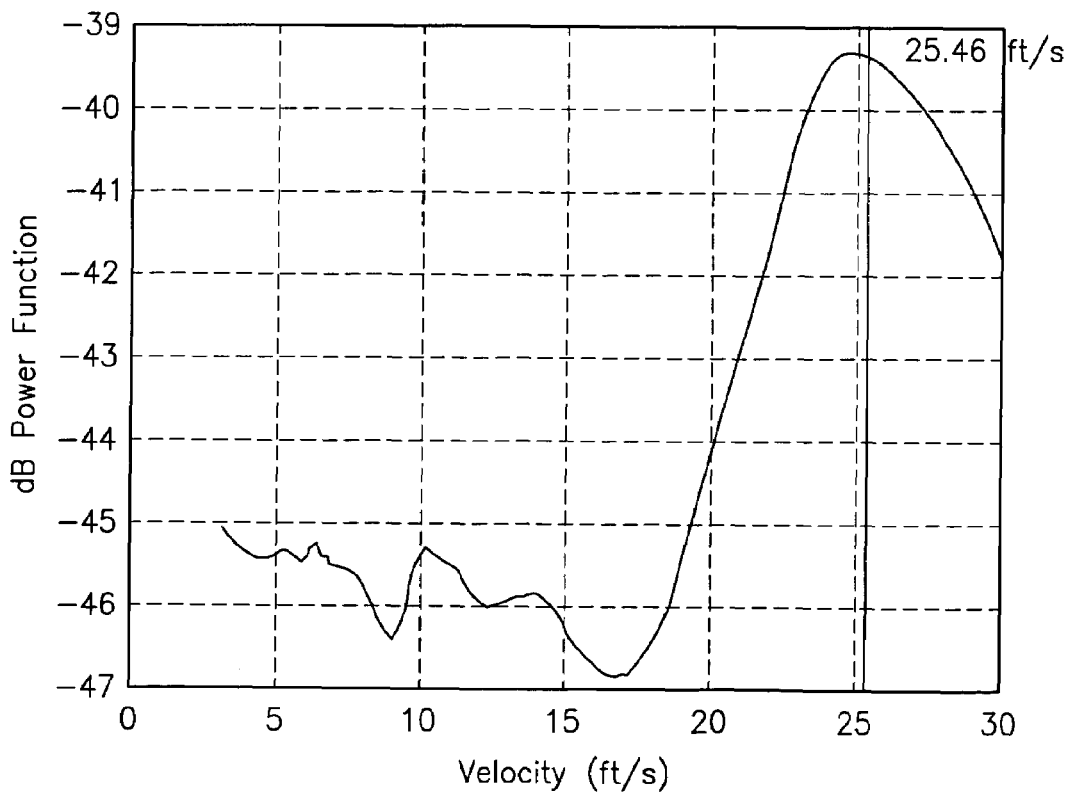
FIG. 13 is a plot of a dB power function versus velocity of the fluid of the k-ω plane for determining the slope having the greatest power which corresponds to the slope of the convective ridge in the k-ω plot of FIG. 12, in accordance with the present invention.

FIG. 12 shows a k-ω plot determined from a flow meter embodying the present invention measuring the flow of pure water and entrained air flowing within a 2 inch pipe. The flow meter, similar to that shown in FIG. 1, is configured as a through transmission configuration and is measuring time of flight of the ultrasonic signals through the fluid. The sensing device comprises eight (8) sensing units 18-21 spaced axially 1.2 inches apart. The sensors 40,42 include 5 MHz transducers. FIG. 13 illustrates the dB power function of the k-ω plot or plane shown in FIG. 12, which shows a flow rate of 25.46 ft/sec.

Figure 14:
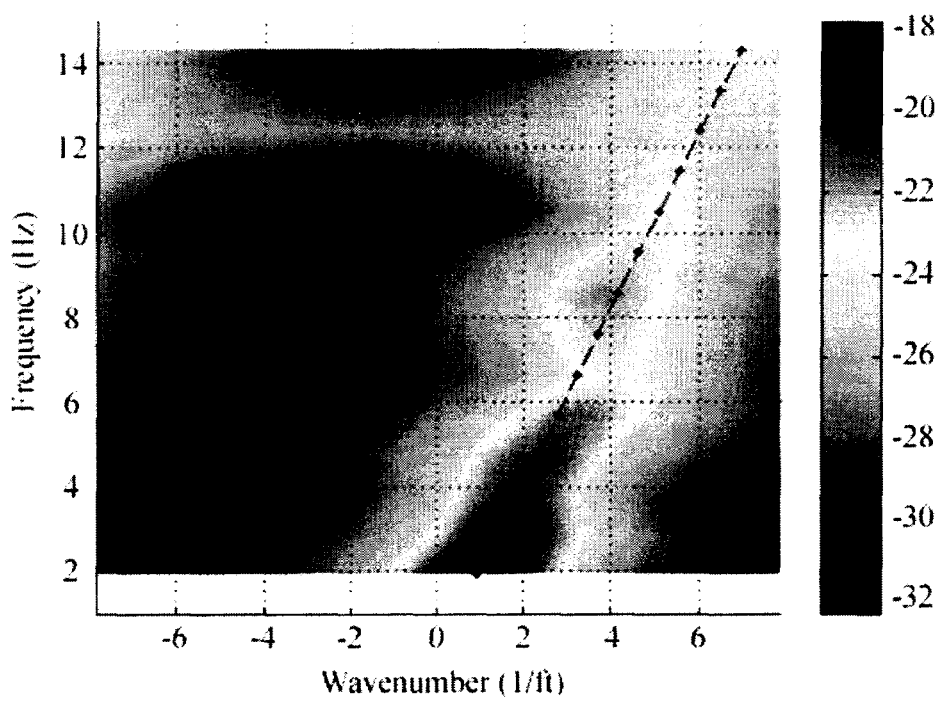
FIG. 14 is a k-ω plot constructed according to the present invention using a time of flight measurement, showing a convective ridge, wherein the fluid flowing in a pipe is a pulp slurry having 4.3% consistency.
Figure 15:
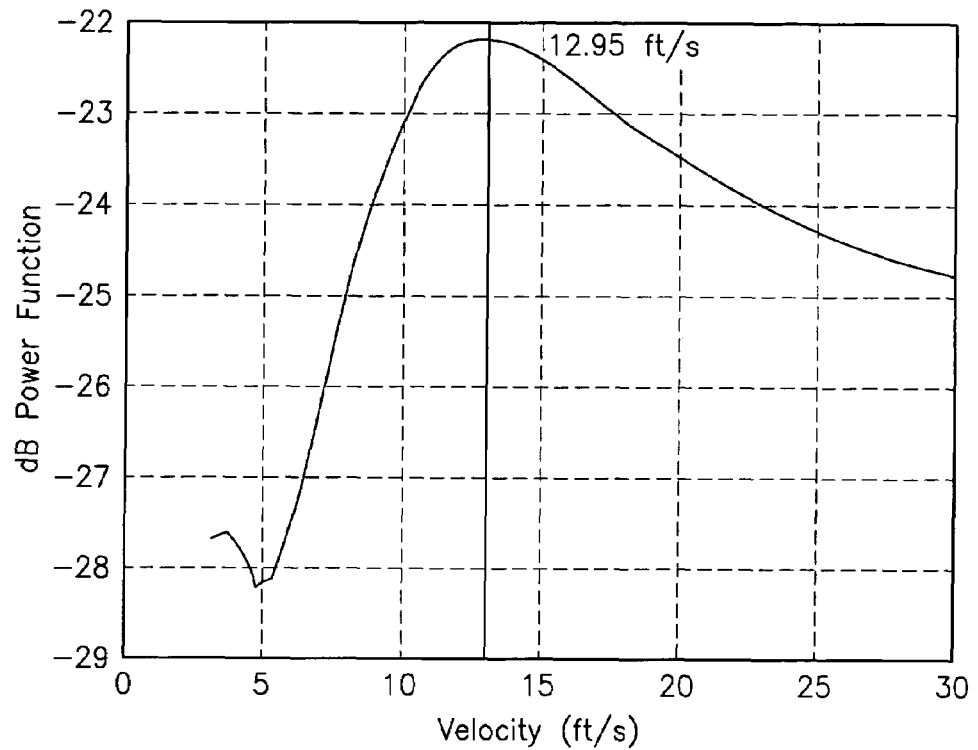
FIG. 15 is a plot of a dB power function versus velocity of the fluid of the k-ω plane for determining the slope having the greatest power which corresponds to the slope of the convective ridge in the k-ω plot of FIG. 14, in accordance with the present invention.

FIG. 14 shows a k-ω plot determined from a flow meter embodying the present invention measuring the flow of 4.3% consistency pulp/paper slurry within an 8 inch pipe. The flow meter, similar to that shown in FIG. 1, is configured as a through transmission configuration and is measuring time of flight of the ultrasonic signals through the fluid. The sensing device comprises two (2) sensing units 18-21 spaced axially 1.2 inches apart. The sensors 40,42 include 1 MHz transducers. FIG. 15 illustrates the dB power function of the k-ω plot or plane shown in FIG. 14, which shows a flow rate of 12.95 ft/sec.

Figure 16:
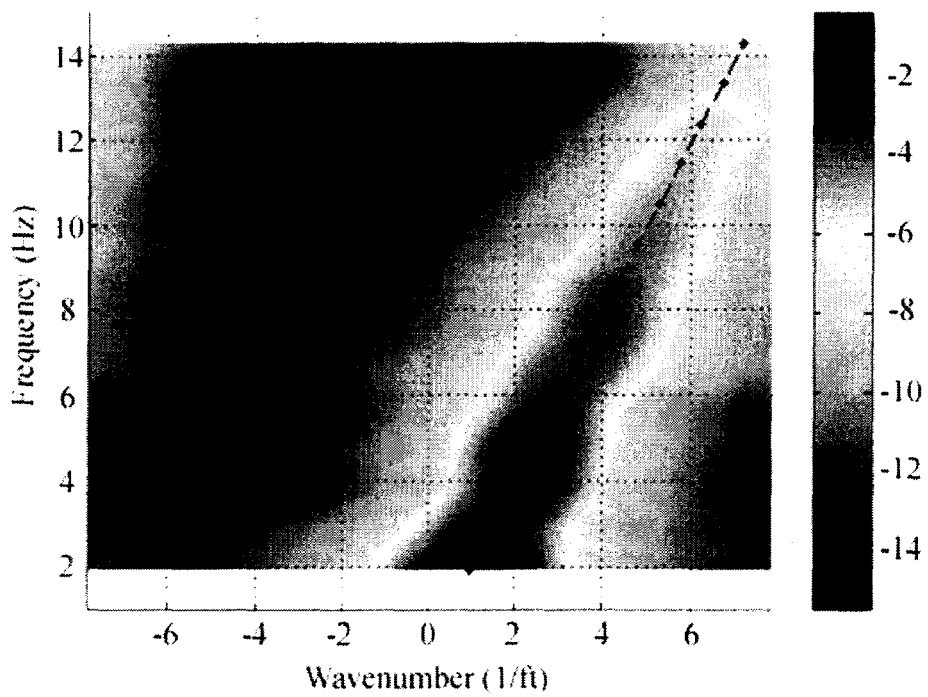
FIG. 16 is a k-ω plot constructed according to the present invention using an amplitude measurement, showing a convective ridge, wherein the fluid flowing in a pipe is a pulp slurry having 4.3% consistency.
Figure 17:
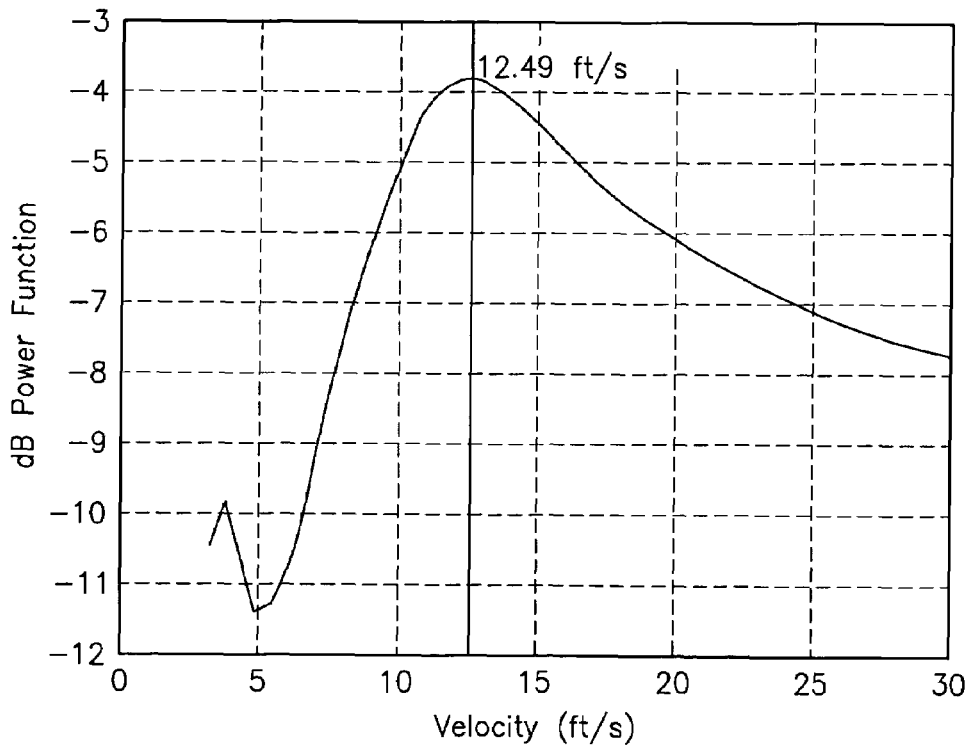
FIG. 17 is a plot of a dB power function versus velocity of the fluid of the k-ω plane for determining the slope having the greatest power which corresponds to the slope of the convective ridge in the k-ω plot of FIG. 16, in accordance with the present invention.

FIGS. 16 shows a k-ω plot determined from a flow meter embodying the present invention measuring the flow of 4.3% consistency pulp slurry within an 8 inch pipe. The flow meter, similar to that shown in FIG. 1, is configured as a through transmission configuration and is measuring the amplitude (e.g., amplitude attenuation) of the ultrasonic signals through the fluid. The sensing device comprises two (2) sensing units 18-21 spaced axially 1.2 inches apart. The sensors 40,42 include 1 MHz transducers. FIG. 17 illustrates the dB power function of the k-ω plot or plane shown in FIG. 16, which shows a flow rate of 12.49 ft/sec.

Figure 18:
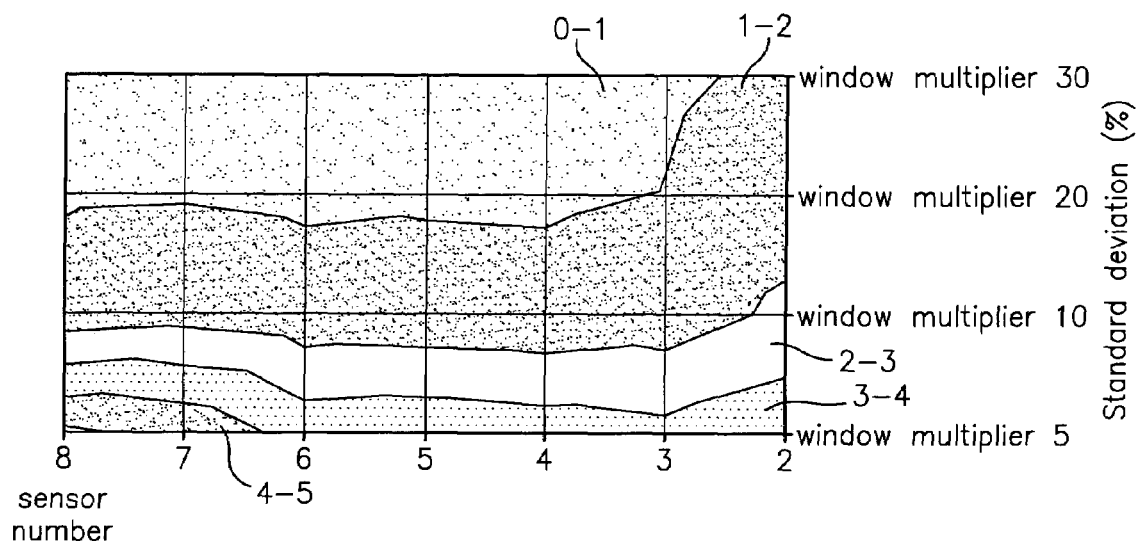
FIG. 18 is a plot of the standard deviation of the output measurement of a flow meter embodying the present invention during low vibration conditions as a function of the number of sensor units in the array and the window multiplier.

FIG. 18 is a plot of the standard deviation of the output measurement of a flow meter embodying the present invention similar to that shown in FIG. 1 during low vibration conditions as a function of the number of sensor units 18-21 in the array 16 and the window multiplier. The flow meter measured water flowing through an 8 inch pipe having a flow rate of 3 ft/sec. The spacing between the sensor units 18-21 of the sensing device 16 was 1.2 inches. The naturally occurring random vibration of the pipe had an acceleration of 103 dB.

Figure 19:
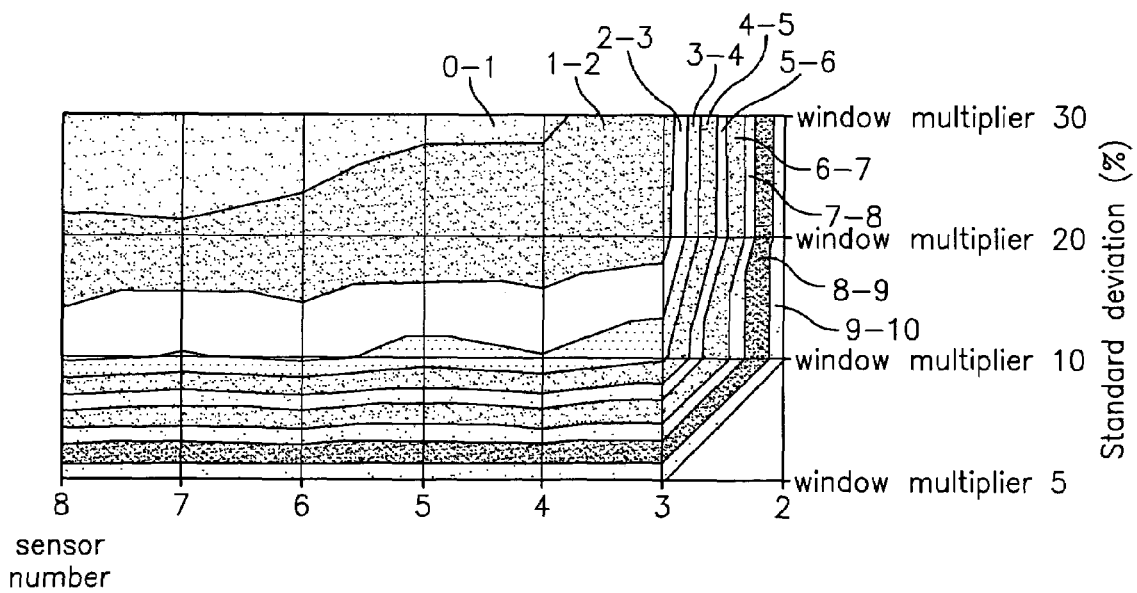
FIG. 19 is a plot of the standard deviation of the output measurement of a flow meter embodying the present invention during high vibration conditions as a function of the number of sensor units in the array and the window multiplier.

The window multiplier is indicative of the amount of time each sensing unit 18-21 collects data before processing the information. This time period equates to an update period of the flow meter. This total time of sampling is defined by the following relationships:

Total Time of sampling=(Window Multiplier)$t$ wherein $t=\Delta x/u$. $\Delta x$ is the spacing of the sensing units, u is the velocity of the flow FIG. 19 is a plot of the standard deviation of the output measurement of a flow meter embodying the present invention similar to that shown in FIG. 1 during hi vibration conditions as a function of the number of sensor units 18-21 in the array 16 and the window multiplier. The flow meter measured water flowing through an 8 inch pipe having a flow rate of 3 ft/sec. The spacing between the sensor units 18-21 of the sensing device 16 was 1.2 inches. A vibrator vibrated the pipe at an acceleration of 132 dB with a random vibration spectrum similar to that measured in field applications.

As one can see, this data illustrates that the ultrasonic flow meter 10 of the present invention is very robust under high vibration conditions. High accuracy of the flow meter can be achieve by using a greater number of sensing units 18-21 and providing a longer sampling time for the sensing device.

While the ultrasonic sensors 40,42 of each sensor unit 18-21 is shown and described as being diametrically opposed, the present invention contemplates that each corresponding sensor 40,42 may simple oppose each other on the pipe and is not limited to being disposed at the diameter of the pipe. Further the opposing sensors 40,42 (not diametrically) may also be positioned such the ultrasonic signal propagating therebetween is orthogonal to the direction of the flow.

While the embodiments of the present invention described hereinbefore show that the array of ultrasonic sensors are disposed in the same plane, the present invention contemplates that the sensor units 18-21 may be at different radial location on the pipe compared to each other.

Sonar-based flow measurement methods have been developed that utilizes strain-based sensors to provide a measurement of a property that convects with the flow. For turbulent Newtonian fluids, the pipe deflects as a result of the pressure perturbation generated by the coherent vortical disturbances. There are many other mechanisms that result in a coherent disturbance convecting with the flow as observed by the clamp-on strain sensor array. By direct analogy, ultrasonic sensors that measure the transit time at a given axially location will provide a measure of the many properties that convect with the flow.

While the sonar-based flow measurement methods using strain based sensors operate well in specific applications, this measurement method is not as robust as using ultrasonic sensors under certain conditions. Using ultra-sonic sensors 40,42 with sonar-based flow measurement provides an accurate robust flow meter that can operate at higher temperatures, higher vibration levels and in higher acoustic noise. Consequently, the ultrasonic meter can measure at lower flow rates and provide faster processing time as shown above. The ultrasonic meter also has higher signal to noise on most types of fluids.

While the present invention describes a flow meter having an array of ultra-sonic meters to measure the velocity of the vortical disturbances within the flow 12, the present invention contemplates that the ultra-sonic sensors 18-21 measures any property and/or characteristic of the flow 12 that convects with the flow (e.g., vortical disturbances, inhomogenieties within the flow, temperature variations, acoustic wave variations propagating within the pipe, bubbles, particles, pressure disturbances).

While the present invention uses a pair of ultrasonic sensors 40,42 to measure the transit time or time of flight of an ultrasonic signal propagating therebetween, the present invention contemplates that the pair of ultrasonic sensors provides a signal indicative of the power or amplitude of the ultrasonic signal propagating therebetween. In other words for amplitude variations, the output signal is indicative of the varying attenuation (or amplitude) of the ultrasonic signal caused by the substances in the fluid flow, such as bubbles, particles, and/or other substances that will vary the amplitude of the ultrasonic signals.

While the ultrasonic sensor units 52, 54 and 18-21 of FIG. 1 comprises a pair of ultrasonic sensors 40,42 (transmitter and receiver), the present invention contemplates a sensing unit comprising one ultrasonic sensor that transmits an ultrasonic signal through the pipe wall and fluid substantially orthogonal to the direction of flow and receives a reflection of the ultrasonic signal reflected back to the ultrasonic sensor.

Further, the present invention contemplates other sensors that can measures parameters that convect with the flow 12, such as temperature sensors, magnetic sensors, capacitive sensors, inductive sensor, optical sensors, and laser-based sensors.

While the present invention contemplates sensors 40,42 that are clamped to the outer surface of the pipe including ultrasonic sensors that do not contact the fluid, the present invention contemplates that the sensors may be "wetted" or in contact with fluid. Further, the sensors may be integral or not easily removable from the pipe, such as a spool piece, or separate unit other than the process piping.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

It is to be understood that the above-described arrangements are only illustrative of the application of the principles of the present invention. Numerous other modifications and alternative arrangements may be devised by those skilled in the art without departing from the spirit and scope of the present invention, and the appended claims are intended to cover such modifications and arrangements.

What is claimed is:

1. An apparatus for measuring the flow velocity of a liquid flowing through a conduit, the apparatus comprising:

an array of ultrasonic sensor pairs disposed at locations spaced along the length of the conduit in the direction of the flow of the liquid, each ultrasonic sensor pair having an ultrasonic transmitter and an ultrasonic receiver, each ultrasonic transmitter providing an ultrasonic signal having a transmission frequency of at least 5 megahertz, each ultrasonic receiver being responsive to the receipt of the ultrasonic signal for providing a respective sensor signal indicative of a parameter of an ultrasonic signal propagating through the liquid, wherein the array of ultrasonic sensor pairs comprising 4, 5, 6, 7, 8, 9, 10, 11, 12, 13, 14, 15, or 16 ultrasonic sensor pairs; and a processor that performs a spatial-temporal transformation to define a convective ridge from the x-t domain to the k-ω domain in response to the sensor signals, and determines the slope of at least a portion of the convective ridge representing a concentration of disturbances that convect with the flow to determine the flow velocity of the liquid.

2. The apparatus of claim 1, wherein the processor samples the sensor signals over a predetermined time period, accumulates the sampled sensor signals over a predetermined sampling period, and processes the sampled sensor signals to define the convective ridge in the k-ω domain.

3. The apparatus of claim 1, wherein the processor further determines the orientation of the convective ridge in the k-ω domain.

4. The apparatus of claim 1, wherein the sensor signals are indicative of vortical disturbances with the liquid.

5. The apparatus of claim 1, wherein the processor uses a beam forming algorithm to define the convective ridge in the k-ω domain.

6. The apparatus of claim 1, wherein the processor determines the slope of at least a portion of the convective ridge by approximating the convective ridge as a straight line.

7. The apparatus of claim 1, wherein the processor further determines the volumetric flow rate of the liquid.

8. The apparatus of claim 1, wherein the parameter of the sensor signals is the transit time to propagate through the liquid between each ultrasonic sensor pair.

9. The apparatus of claim 1, wherein the parameter of the sensor signals is the amplitude of the sensor signals.

10. The apparatus of claim 1, wherein the ultrasonic sensor pairs are clamped onto an outer surface of the conduit.

11. The apparatus of claim 1, wherein the ultrasonic sensor pairs are attached to the conduit.

12. The apparatus of claim 1, wherein the ultrasonic transmitter and the ultrasonic receiver of each ultrasonic sensor pair are disposed opposing each other such that the ultrasonic signal propagates through the liquid substantially orthogonal to the direction of the liquid flow.

13. The apparatus of claim 1, wherein the processor uses an array processing algorithm.

14. The apparatus of claim 5, wherein the beam forming algorithm includes one of a Capon algorithm and a MUSIC algorithm.

15. The apparatus of claim 11, wherein the ultrasonic sensor pairs are in contact with the liquid.

* * * * *